United States Patent
Blatt et al.

(10) Patent No.: US 7,909,878 B2
(45) Date of Patent: Mar. 22, 2011

(54) ARTIFICIAL SPINAL DISC, INSERTION TOOL, AND METHOD OF INSERTION

(76) Inventors: Geoffrey Blatt, Overland Park, KS (US); Eric Blatt, Alexandria, VA (US)

( * ) Notice: Subject to any disclaimer, the term of this patent is extended or adjusted under 35 U.S.C. 154(b) by 275 days.

(21) Appl. No.: 11/856,620

(22) Filed: Sep. 17, 2007

(65) Prior Publication Data

US 2008/0009881 A1   Jan. 10, 2008

Related U.S. Application Data

(62) Division of application No. 10/973,795, filed on Oct. 26, 2004, now Pat. No. 7,338,527.

(51) Int. Cl.
*A61F 2/44* (2006.01)
*A61B 17/70* (2006.01)
*A61B 17/60* (2006.01)

(52) U.S. Cl. .................. 623/17.15; 606/99; 606/86 A

(58) Field of Classification Search .... 623/17.11–17.16; 606/86 A, 86 R, 90–94, 96–99, 279
See application file for complete search history.

(56) References Cited

U.S. PATENT DOCUMENTS

| | | | | |
|---|---|---|---|---|
| 4,335,715 A * | 6/1982 | Kirkley | ............................. | 606/87 |
| 4,535,768 A * | 8/1985 | Hourahane et al. | ......... | 606/86 R |
| 4,566,466 A | 1/1986 | Ripple et al. | | |
| 4,672,957 A * | 6/1987 | Hourahane | ...................... | 606/80 |
| 4,722,331 A * | 2/1988 | Fox | ................................ | 606/96 |
| 5,562,736 A | 10/1996 | Ray et al. | | |
| 5,674,296 A | 10/1997 | Bryan et al. | | |
| 5,697,977 A * | 12/1997 | Pisharodi | ....................... | 606/279 |
| 5,906,616 A * | 5/1999 | Pavlov et al. | ................. | 606/247 |
| 6,039,763 A | 3/2000 | Shelokov | | |
| 6,120,511 A * | 9/2000 | Chan | .............................. | 606/96 |
| 6,132,464 A | 10/2000 | Martin | | |
| 6,482,237 B2 * | 11/2002 | Mosseri | ..................... | 623/22.12 |
| 6,485,518 B1 * | 11/2002 | Cornwall et al. | .......... | 623/17.11 |
| 6,530,929 B1 | 3/2003 | Justis et al. | | |
| 6,641,614 B1 * | 11/2003 | Wagner et al. | ............. | 623/17.15 |
| 6,740,087 B2 * | 5/2004 | Knox | .......................... | 606/86 A |
| 6,969,392 B2 * | 11/2005 | Gitis et al. | ...................... | 606/87 |
| 6,972,019 B2 * | 12/2005 | Michelson | .................. | 606/86 A |
| 7,485,120 B2 * | 2/2009 | Ray | .................................. | 606/87 |
| 7,527,629 B2 * | 5/2009 | Link et al. | ....................... | 606/87 |
| 2002/0029039 A1 | 3/2002 | Zucherman et al. | | |
| 2002/0156473 A1 | 10/2002 | Bramlet et al. | | |
| 2003/0135277 A1 * | 7/2003 | Bryan et al. | ................ | 623/17.12 |
| 2004/0148028 A1 * | 7/2004 | Ferree et al. | ............... | 623/17.11 |
| 2004/0210314 A1 * | 10/2004 | Michelson | ................. | 623/17.16 |
| 2004/0220567 A1 * | 11/2004 | Eisermann et al. | ............. | 606/61 |
| 2004/0230304 A1 * | 11/2004 | Yuan et al. | ................. | 623/17.11 |
| 2004/0249465 A1 * | 12/2004 | Ferree | ......................... | 623/17.16 |
| 2005/0010294 A1 * | 1/2005 | Michelson | ................. | 623/17.11 |
| 2005/0038516 A1 * | 2/2005 | Spoonamore | .............. | 623/17.14 |

(Continued)

*Primary Examiner* — Thomas C Barrett
*Assistant Examiner* — Matthew Lawson

(57) ABSTRACT

An artificial spinal disc is provided for unilateral insertion from the posterior side of the patient and includes a pair of plate members with a bearing associated with one plate member and a depression associated with the other for permitting limited flexibility of patient movement. An outrigger is provided which includes rods extending through the pedicles on one side of each of two adjacent vertebrae and posts connected to the rods which provide an artificial facet joint. A method of insertion of the artificial spinal disc hereof includes cutting channels for receiving longitudinally extending ribs on the plate members and removing the natural facet joint in order to permit insertion of the artificial spinal disc. A tool for insertion of the artificial spinal disc acts as a drill guide for creating a passage through the pedicles.

9 Claims, 10 Drawing Sheets

U.S. PATENT DOCUMENTS

| | | | |
|---|---|---|---|
| 2005/0143818 A1* | 6/2005 | Yuan et al. | 623/17.11 |
| 2005/0203532 A1* | 9/2005 | Ferguson et al. | 606/90 |
| 2005/0209694 A1* | 9/2005 | Loeb | 623/17.11 |
| 2005/0216081 A1 | 9/2005 | Taylor | |
| 2005/0234449 A1* | 10/2005 | Aferzon | 606/61 |
| 2005/0256578 A1 | 11/2005 | Blatt et al. | |
| 2006/0085010 A1* | 4/2006 | Lieberman | 606/99 |
| 2009/0062921 A1* | 3/2009 | Michelson | 623/17.16 |

\* cited by examiner

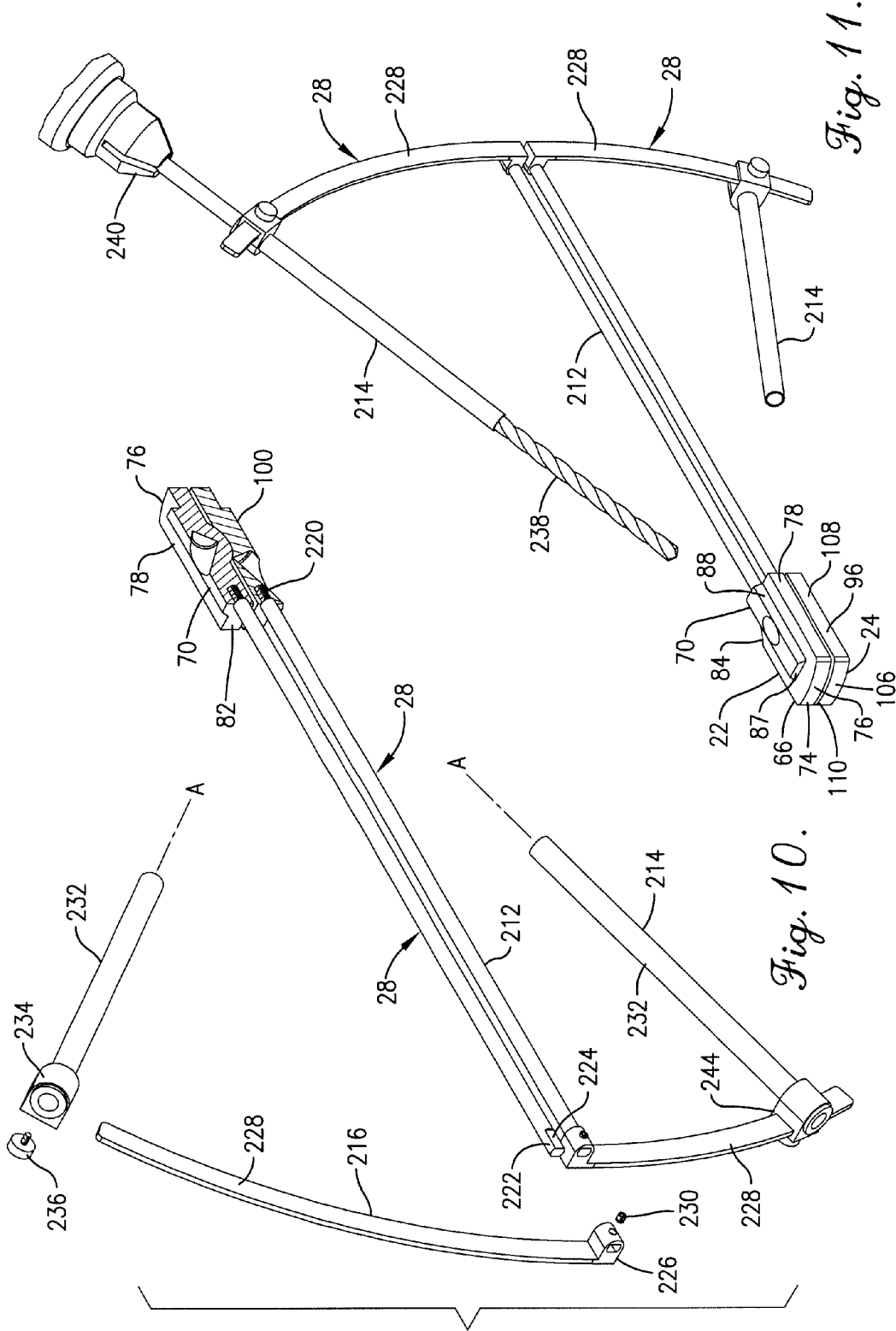

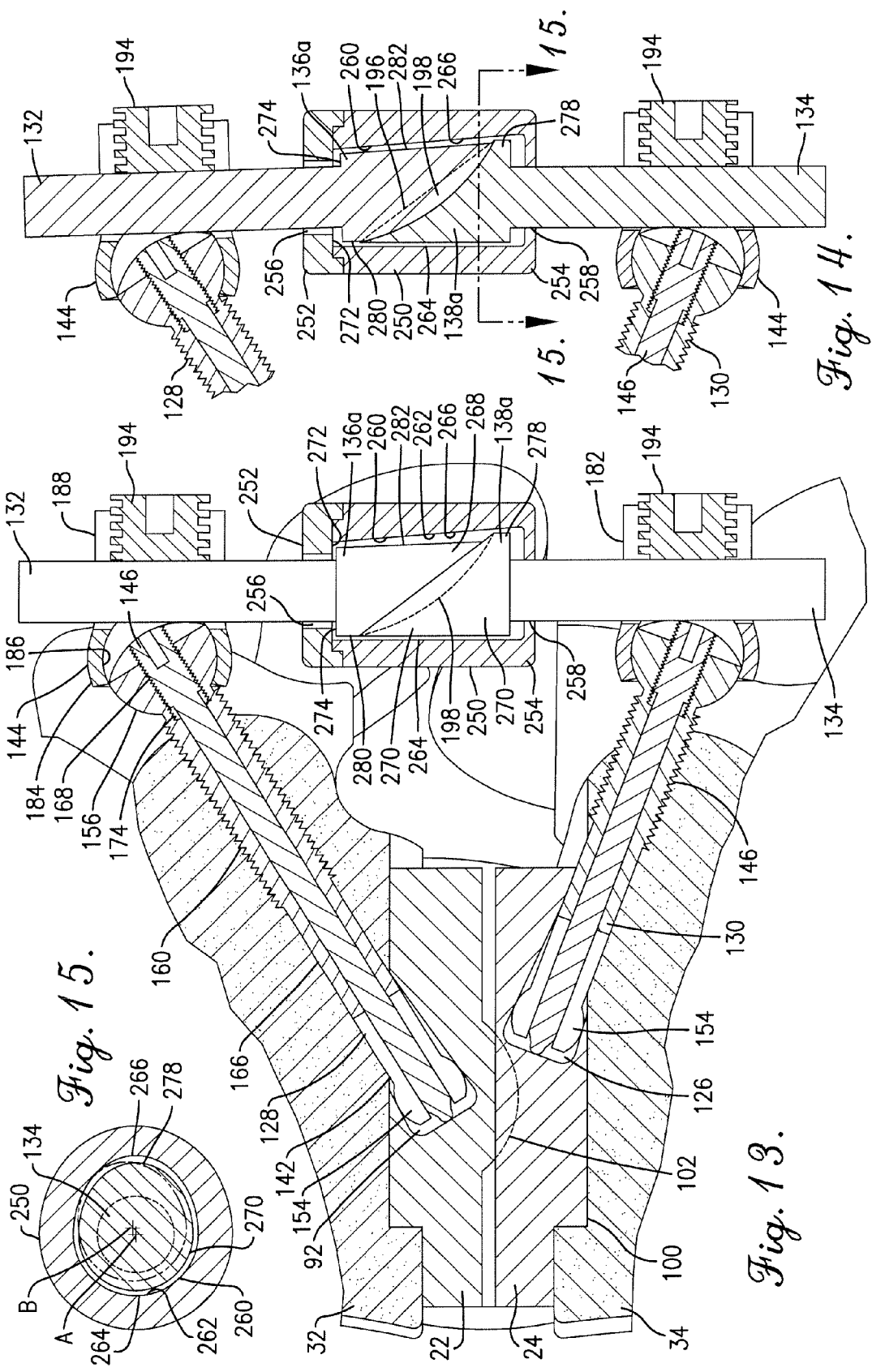

ARTIFICIAL SPINAL DISC, INSERTION TOOL, AND METHOD OF INSERTION

RELATED APPLICATION

This application is a divisional application of U.S. patent application Ser. No. 10/973,795, filed Oct. 26, 2004, incorporated by reference herein.

BACKGROUND OF THE INVENTION

1. Field of the Invention

This invention broadly concerns an artificial disc, insertion tool, and method of insertion for treating conditions of the human spine. More particularly, it is concerned with providing a system and method which advantageously permits insertion of the artificial disc from the posterior region of the patient and provides a unilateral approach with posterior stabilization through fixation through the pedicles of the vertebrae while still allowing the patient to enjoy a range of motion in the area of the artificial disc.

2. Description of the Prior Art

A number of conditions can result in damage or deterioration of one or more intervertebral discs of the human spine (hereinafter "discs"). A disc may become damaged by external injury or degenerative disc disease due to advanced age in combination with other factors, just to mention two examples. One condition which results in significant pain and potential nerve damage, and may require surgery, is a herniated disc.

One type of surgery which has benefitted patients with disc problems is fusion of the vertebrae adjacent the disc. In this surgery, the natural disc is replaced with a spacer and the vertebrae are fixed relative to one another. While such surgery provides a degree of relief to the patient, it necessarily limits flexibility of the spine, which presents a disadvantage for patients with an active lifestyle. Another disadvantage is the placement of greater loads on the adjacent vertebrae, resulting in what is commonly known as "adjacent segment disease." Later efforts in the treatment of human disc problems is the use of artificial human discs. Conventionally, this treatment involves the removal of the natural human disc and the insertion of two plates through the abdomen, i.e. the anterior side of the patient. The reason that insertion through the anterior of the patient is thought to be the conventional method is that it avoids the necessity of passing the artificial disc past one or more of the spinal facets or articular processes, or the spinal cord. These body parts present significant obstacles to attempts to insert an artificial disc posteriorly. One problem with such conventional disc replacement systems and methods is that the anterior insertion of the disc does necessitate surgical involvement of the two major blood vessels, the vena cava and the aorta. Anterior insertion requires spreading the abdominal muscles and the aorta and vena cava in order to gain access to the vertebrae and the disc. Because rupture of either of the vena cava or aorta is life-threatening, such surgery requires the attendance of both a vascular surgeon as well as a spinal surgeon. Another problem is the difficulty presented in providing artificial discs in two pieces which provide satisfactory support and balance along a single load bearing point as close to the center load line of the spine as possible.

As a result, there has developed a need for an improved artificial disc which may be inserted unilaterally from the posterior side of the patient.

Moreover, there has developed a need for an improved artificial disc which provides support for the spinal column while providing the desired flexibility of movement.

Furthermore, there is a need for an improved artificial disc which minimizes the risk of injury to the patient during the surgical process.

In addition, there is a need for an improved method of insertion of an artificial disc which reduces the potential risk to the patient during surgery, minimizes or eliminates the necessity of spreading the abdominal muscles, and yet provides satisfactory insertion and stabilization of the disc.

SUMMARY OF THE INVENTION

These and other objects will be largely met by the artificial spinal disc, insertion tool and method of insertion of the present invention. That is to say, the present invention provides a device which is particularly designed for posterior insertion, and further provides insertion in a unilateral direction, while being minimally invasive to the patient. In this regard, only a portion of the patient's natural disc needs to be removed to receive the new artificial disc hereof.

Broadly speaking, the present invention includes an artificial disc which includes two opposing plate members each having an outrigger which includes a facet to replace the natural facet joint between the inferior articular process of one vertebra and the superior articular process of the adjacent vertebra. Portions of these inferior and superior articular processes are removed during the surgery to permit insertion of the plates from one side of the posterior position of the vertebra. The plate members are complementally configured to permit limited relative motion therebetween. They are also particularly configured with the ribs substantially centered longitudinally and provided with a recess in the ribs to enable mounting of the outriggers. Further, the plate members include a rounded nose configured complementally with the cross-sectional curvature of the natural disc and a relieved edge configured to avoid involvement with the spinal cord. One of the plate members is thus preferably provided with a convex portion which faces a convex portion of the opposing plate member. Ribs extend along the opposite surfaces of the plate members for limiting lateral motion of the plate members once inserted, and permit a unilateral insertion of the plate members between the adjacent vertebrae. The plate members may beneficially be provided with a bio-ingrowth surface to promote bone growth and thus more secure attachment to the vertebra. The outriggers include rods extending through the pedicles of the vertebrae which are attached to the plate members. In addition, the outriggers include respective superior and inferior posts connected to the respective rods, and facet heads on each post which are complementally configured to permit limited relative movement therebetween. The outriggers serve as artificial facets to replace the facet joint between the articular processes removed during surgery, so that support for the patient's spine is not compromised by removal of one of the facets of the vertebra. The other facet of the vertebra can also be replaced if desired using pedicle screws or a second attachment to the plate members of the artificial disc. The artificial facets may be enclosed in a flexible skirt, or alternatively a rigid collar can be provided in surrounding relationship to the artificial facets to help maintain the facets in proximity and further limit the amount of relative movement between the facets.

The present invention also beneficially provides for the cut for receiving and locating the plate members to be made along a single line of insertion—i.e. unilaterally—from generally the posterior of the patient. The provision for a unilateral cut through the natural disc and along each of the adjacent vertebrae provides a good support against lateral movement of the plate members, a favorable interface with the bone, leaves a portion of the natural disc intact for support and cushioning, and makes it easier for the surgeon to make the right cut and avoid errors.

The invention hereof also includes a novel tool for use during attachment of the outriggers. The tool functions as a guide for use in drilling the channel through the pedicles for receiving the outrigger rods. The tool, which includes a carrier and a drill guide, is advantageously temporarily mounted on one of the plate members and then the other, or two such tools can be employed simultaneously, so that the channel which is drilled is related to the position of the plate members after insertion into the spine, and more particularly the opening into the recess of the plate members. Moreover, the tool is adjustable whereby the surgeon can accommodate variations in individual physiology so that the channel is most advantageously located for the patient. The drill guide is preferably tubular in configuration, having a central axis, and beneficially the central axis intersects at a common point—the opening to the recess of the plate members—when the guide is shifted on the carrier so that the channel created by the drill remains aligned with the opening into which a part of the outrigger is inserted into the plate member.

The present invention also includes an improved method of insertion of an artificial disc into a patient. Broadly speaking, the method includes cutting a passage through the natural disc and respective slots in adjacent vertebrae from a generally posterior position of the patient, removing at least a part of one of the spinal superior articular processes and at least a part of one of inferior articular processes on the adjacent vertebra. The surgeon then inserts the plate members along the slots in a unilateral approach, first using a specialized spacer for creating additional space between the adjacent vertebrae, if necessary. This spacer includes a handle and a block fixed thereto, so that the block turns with the handle to which it is affixed. The block is wider in one direction and narrower in a direction perpendicular to the one direction, and preferably is rectangular with rounded corners. The block is inserted into a tunnel cut in the natural disc between adjacent vertebra, with the narrow width of the block oriented on the spinal axis, and then turned so that the wider width is oriented substantially on the spinal axis to increase the spacing between the adjacent vertebrae. The tool used for drilling the channels through the pedicles is then attached in sequence to each of the plate members (or two such tools may be used simultaneously) and the channels are drilled through the pedicles to permit attachment of the outriggers. The rods of the outriggers are then inserted through the channels and connected to their respective plate members, and the posts are affixed and secured to the rods.

It is believed that the present invention will attain the goal of reducing the pain experienced by the patient and restoring most of the original range of motion of the spine. Moreover, it should reduce the risks attendant to anterior insertion of artificial discs whereby the presence of a vascular surgeon will no longer be necessary. These and other benefits will be readily appreciated by those skilled in the art with reference to the drawings and the detailed description set forth below.

BRIEF DESCRIPTION OF THE DRAWINGS

FIG. 10 is an exploded view of the tool for guiding the drill, with the artificial disc plate members shown in partial section;

FIG. 11 is a perspective view of the tool as shown in FIG. 10, and showing a drill inserted in the guide of the tool for drilling the channel into one of the pedicles for receiving the rod;

FIG. 13 is an enlarged vertical sectional view of the artificial disc hereof, showing an alternative configuration of the artificial facets and rigid collar instead of a flexible skirt surrounding the artificial facets, the collar being provided with an arcuate-shaped inner wall and permitting one of the rods to pass through an opening in the collar and move relative to the collar;

FIG. 14 is a fragmentary vertical sectional view of the artificial disc as shown in FIG. 13, wherein the upper facet is turned and shifted downwardly relative to the lower facet; and FIG. 15 is a fragmentary horizontal sectional view taken approximately on line 15-15 of FIG. 14 to illustrate the camming effect into the inner wall of the collar caused when the convex face of the upper facet turns or slides upwardly a sufficient distance relative to the concave face of the lower facet.

DESCRIPTION OF THE PREFERRED EMBODIMENT

Figure 1:
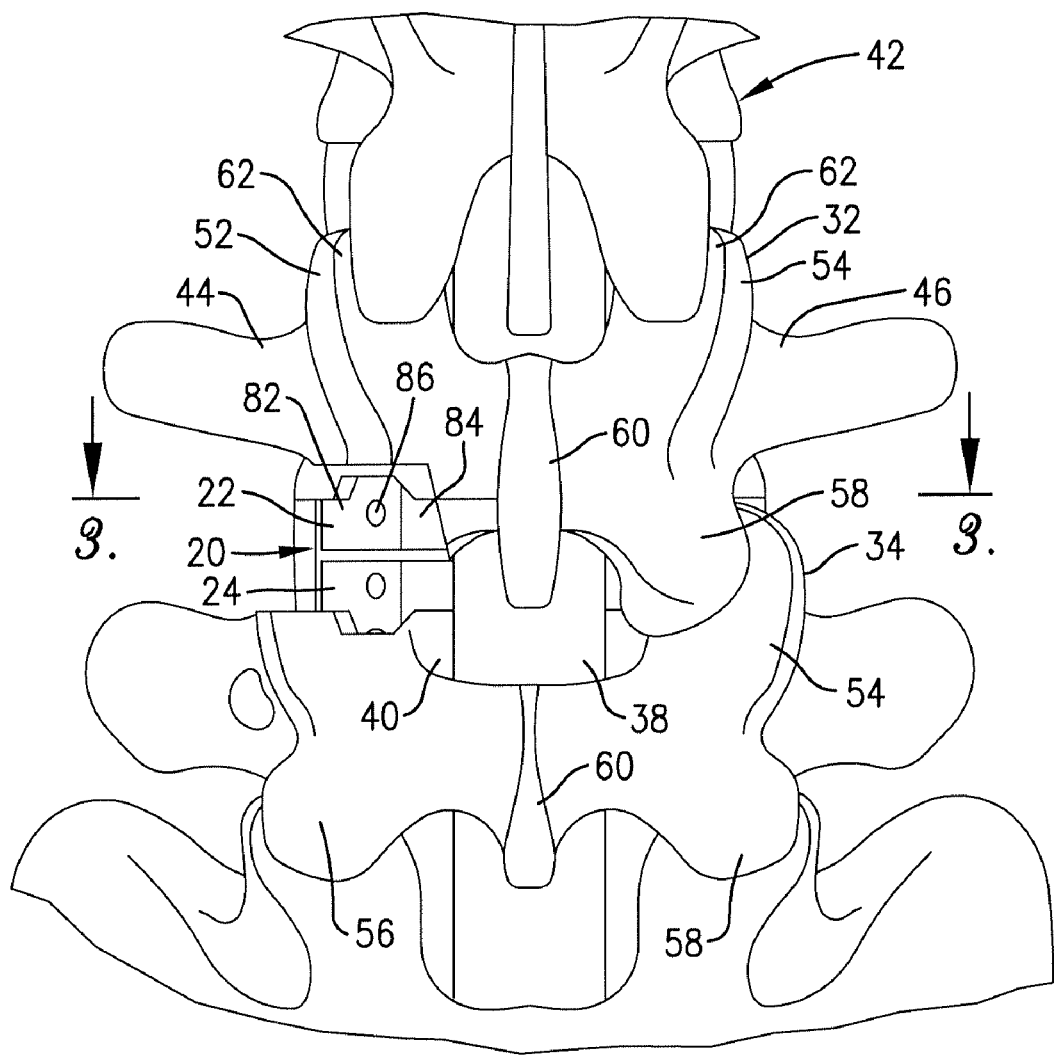
FIG. 1 is a fragmentary rear elevational view of the patient's spine showing the plate members of the artificial disc inserted and the left facet joint removed, but before outriggers of the artificial disc have been attached.
Figure 2:
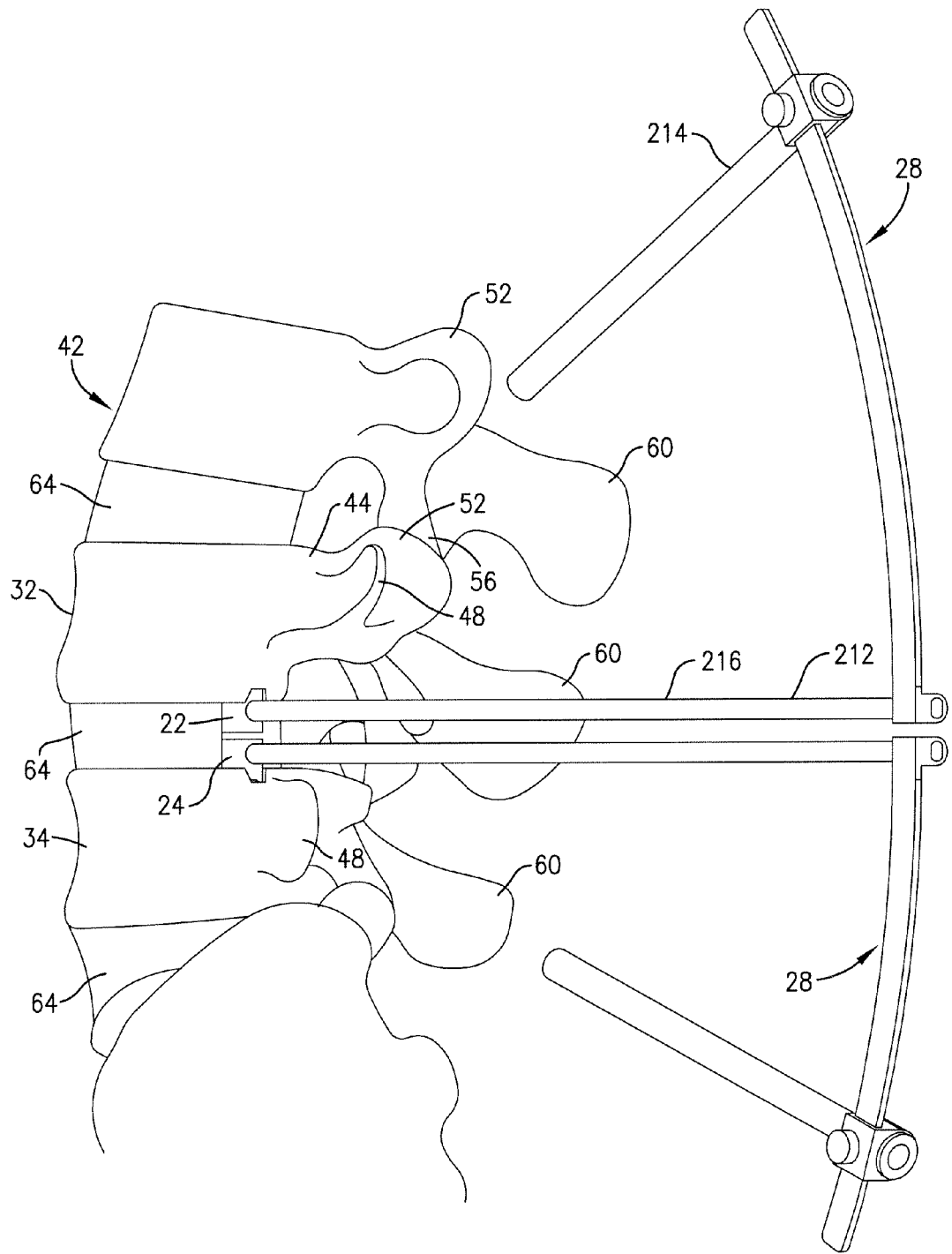
FIG. 2 is a fragmentary side elevational view of the patient's spine showing the plate members of the artificial disc inserted and the tool attached thereto for acting as a drill guide for the channels to receive the outrigger rods.
Figure 3:
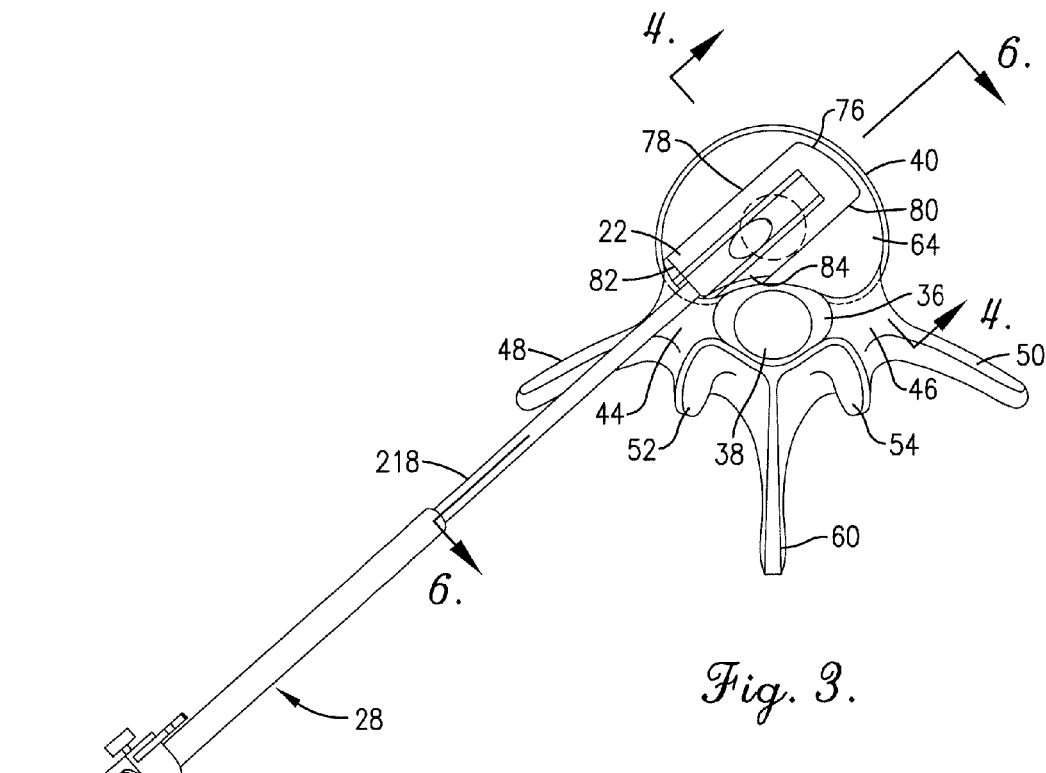
FIG. 3 is a horizontal cross-sectional view taken along line 3-3 of FIG. 1 with portions of adjacent vertebrae removed for clarity, and with an arcuate weight-bearing member of one of the plate members shown in phantom lines, and showing the tool attached to the plate members.
Figure 9:
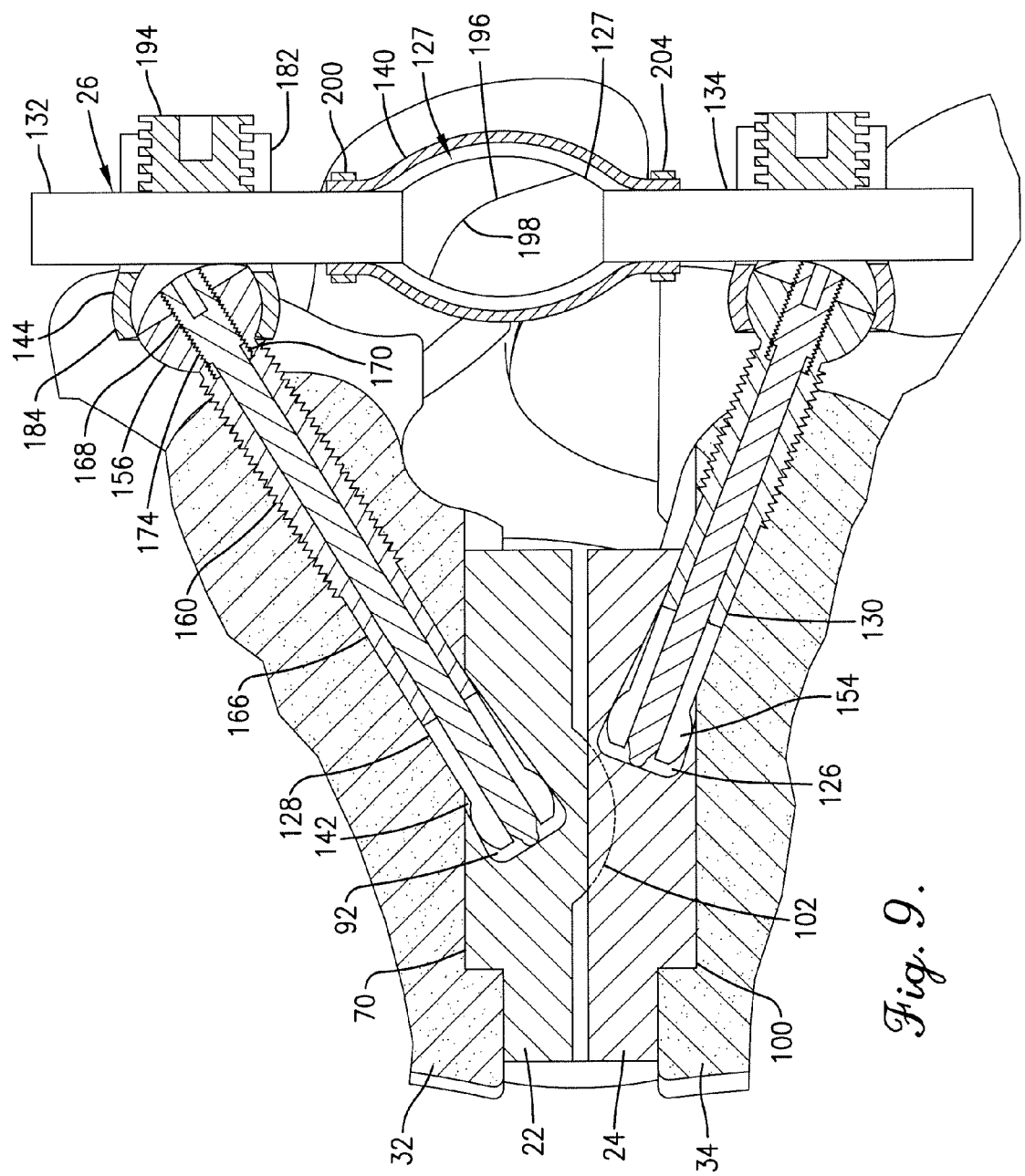
FIG. 9 is an enlarged, fragmentary vertical cross-sectional view similar to FIG. 8, showing the posts with the artificial facet joint thereon coupled to the multiaxial gripping heads on the rods.
Figure 12:
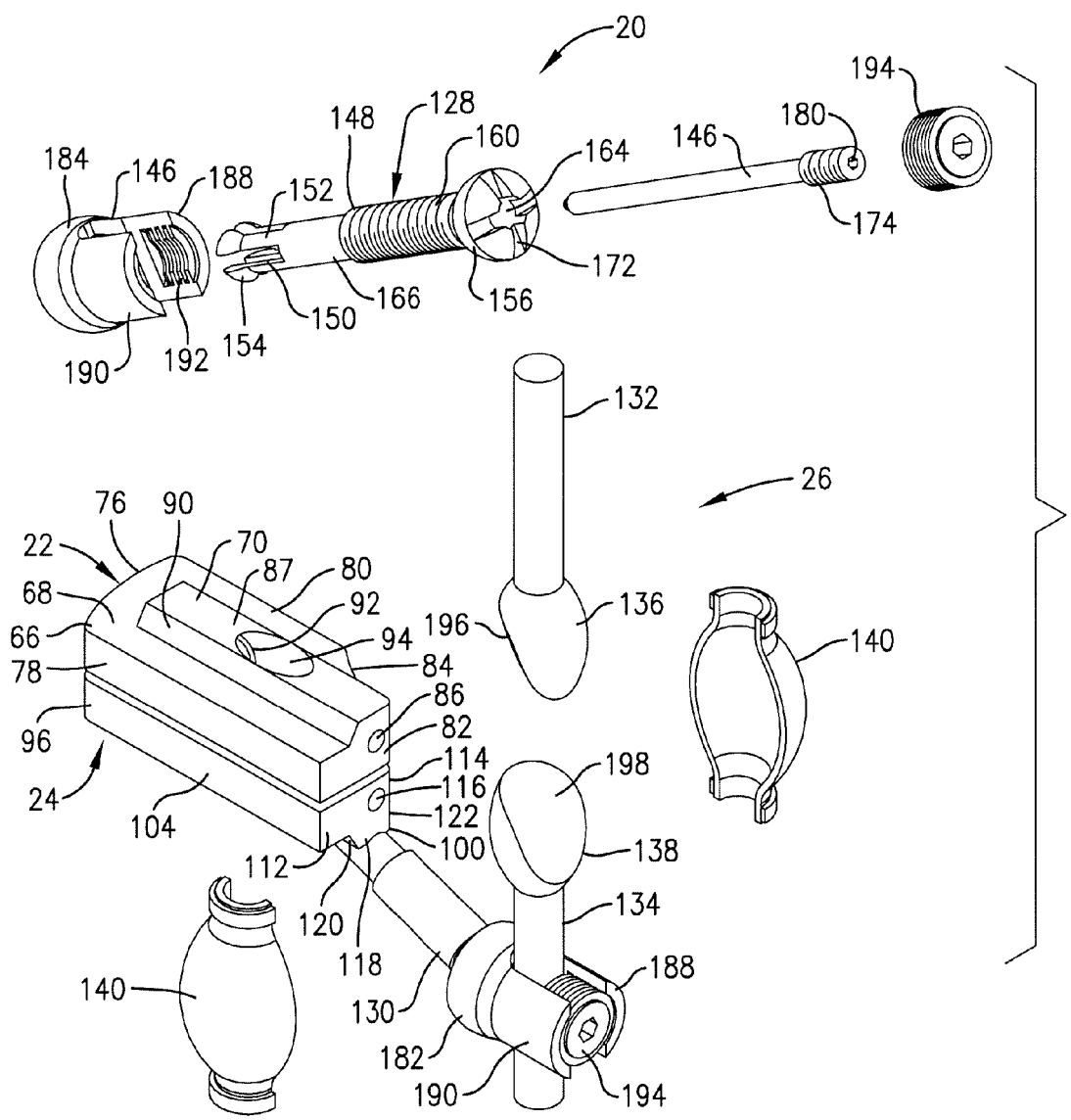
FIG. 12 is an exploded view of the artificial disc, showing the plate members, the rods and posts of the outriggers, and the artificial facet with its casement bisected for clarity.

Referring now to the drawings, an artificial spinal disc 20 in accordance with the present invention is shown in FIGS. 9 and 12 and broadly includes first plate member 22 and second plate member 24 with a connecting outrigger 26. The invention further includes a tool 28 used in drilling channels for receiving the outrigger 26, and a spacer tool 30. The artificial spinal disc 20 is designed for use between adjacent first vertebra 32 and second vertebra 34. As used herein, the terms "first vertebra" and "second vertebra" are used merely as a references to distinguish between two adjacent, superior and inferior vertebra, and not in the medical sense as in "sixth cervical vertebra." As seen in FIGS. 1, 2 and 3 for example, each of the vertebrae 32 and 34 present a vertebral foramen 36 for receiving therein the spinal cord 38, a body 40 which provides a weight bearing capacity for the spinal column 42, left and right pedicles 44 and 46, left and right transverse processes 48 and 50, left and right superior articular processes 52 and 54, left and right inferior articular processes 56 and 58, and a spinous process 60. The inferior articular processes 56 and 58 of first vertebra 32 and the superior articular processes 52 and 54 of second vertebra therebelow work together to provide natural facet joints 62 which provide support and a limited range of movement between the vertebrae. In addition, a natural human disc 64 is located between the first and second vertebra.

In greater detail, the first plate member 22 includes an elongated panel 66 having a first surface 68 for abutment with the first vertebra 32 and a second surface 69 generally facing the second plate member 24 and the second vertebra 34, a longitudinally extending, laterally centered rib 70 extending toward the first vertebra 32 from the first surface 68, and an arcuate, generally convex bearing 72 extending toward the second vertebra 34 from the second surface 34. The panel 66 has a surrounding edge 74 which includes a rounded nose 76, generally straight and relatively parallel side edges 78 and 80, a generally straight back edge 82 extending substantially perpendicular from side edge 78, and relieved edge 84 which is inwardly arcuate and extends from the side edge 80 to the back edge 82. The rounded nose 76 is generally tapered in the longitudinal direction so that when a line is extended perpendicular to the junction of the side edge 78 and the nose 76, the opposite side edge 80 extends past this perpendicular line, as seen in FIG. 3. The rounded nose thus mirrors the rounded anterior margin of the body 40 and the natural disc 64. The relieved edge 84 is recessed to avoid or at least minimize any intrusion of the plate member 22 with the spinal cord. The back edge 82 further includes a longitudinally extending hole 86 which is oriented along the longitudinal axis of the plate member 22 and parallel to the longitudinal extension of the rib 70. The hole 86 is preferably internally threaded for mounting tool 28 thereto, as shown in FIGS. 10 and 11. Bearing 72 is located on second surface 69 in a position not necessarily laterally or longitudinally centered on the panel 66, but rather positioned as shown in FIG. 3 to be centered on what is substantially the weight bearing axis of the spinal column. The plate member 22 may be cast or machined of any suitable metal such as cobalt-chrome stainless steel or titanium, and except for bearing 72, provided with a bio-ingrowth coating or texture, such as, for example, hydroxyappetite or porous beads. Bearing 72 may be cast or machined along with the remainder of the plate member 22 so that it is integrally formed of metal, such as cobalt-chrome stainless steel or titanium, or may be attached to the first surface and provided of a durable and friction-resistant synthetic material such as nylon. The bearing 72 is shown as being domed and semi-hemispherical, but could also be ellipsoid or of other arcuate shapes.

Rib 70 includes a remote surface 87 and a pair of generally angled, divergent (in a direction from the remote surface 87 toward the surface 68) side surfaces 88 and 90. A recess 92 extends in longitudinal alignment into the rib 70 and panel 66. The recess 92 may be cylindrical and/or threaded, but most preferably is generally frustoconical in configuration and has an axis which is angled relative to the remote surface 87 to provide a desired angle of attachment and approach for the outriggers, as seen in FIGS. 6, 7, 8, 9 and 12. The frustoconical shape of the recess 92 is such that an inner wall 94 generally diverges as the depth into the plate member 22 increases.

Plate member 24 shares similar features with plate member 22. In that regard, second plate member 24 includes an elongated panel 96 having a first surface 98 for abutment with the second vertebra 34 and a second surface 99 generally facing the disc 64 and the first vertebra 32, a longitudinally extending, laterally centered rib 100 extending toward the second vertebra 34 from the first surface 98, and an arcuate, generally concave bearing-receiving depression 102 extending inwardly into the panel 96. The panel 96 has a surrounding edge 104 which includes a rounded nose 106, generally straight and relatively parallel side edges 108 and 110, a generally straight back edge 112 extending substantially perpendicular from side edge 108, and relieved edge 114 which is inwardly arcuate and extends from the side edge 110 to the back edge 112. The rounded nose 106 is generally tapered in the longitudinal direction so that when a line is extended perpendicular to the junction of the side edge 108 and the nose 106, the opposite side edge 10 extends past this perpendicular line. Thus, as with panel 66, the rounded nose 106 of the panel 96 thus mirrors the rounded anterior margin of the body 40 and the natural disc 64. The relieved edge 114 is recessed to avoid or at least minimize any intrusion of the plate member 24 with the spinal cord. The back edge 112 further includes a longitudinally extending hole 116 which is oriented along the longitudinal axis of the plate member 24 and parallel to the longitudinal extension of the rib 110. Plate members 22 and 24 are thus designed so that their respective panel edges are substantially congruent when placed in longitudinal alignment in superior-inferior relationship, with the holes 86 and 116 being oriented in parallel relationship. The hole 116, as with hole 86, is preferably internally threaded for mounting tool 28 thereto, as shown in FIGS. 10 and 11. Bearing-receiving depression 102 is located on second surface 99 in a position not necessarily laterally or longitudinally centered on the panel 66, but rather positioned as shown in FIG. 3 to be centered on what is substantially the weight bearing axis of the spinal column. The plate member 22 may be cast or machined of any suitable metal such as cobalt-chrome stainless steel or titanium, and except for bearing-receiving depression 102, provided with a bio-ingrowth coating or texture, such as, for example, hydroxyappetite or porous beads. Bearing-receiving depression 102 has a curvature complemental to the curvature of the bearing 72, but in order to permit rocking of the bearing 72, the depth of the bearing-receiving depression 102 is less than the height of the bearing 72. Thus, the respective surfaces 69 and 99 of panels 66 and 96 have a space S therebetween when the panels are in an initial, parallel orientation. The bearing receiving depression 102 is machined or otherwise formed in the plate member 24 to be smooth, and is preferably integrally formed of metal, such as cobalt-chrome stainless steel or titanium. If desired, a friction-resistant coating of lining of a durable and friction-resistant synthetic material such as nylon may be provided.

Rib 100 includes a remote surface 118 and a pair of generally angled, divergent (in a direction from the remote surface 118 toward the surface 98) side surfaces 120 and 122. A recess 124 extends in longitudinal alignment into the rib 110 and panel 96. The recess 124 may be cylindrical and/or threaded, but most preferably is generally frustoconical in configuration and has an axis which is angled relative to the remote surface 118 to provide a desired angle of attachment and approach for the outriggers, as seen in FIGS. 6, 7, 8, 9 and 12. The frustoconical shape of the recess 124 is such that an inner wall 126 generally diverges as the depth into the plate member 24 increases.

Outrigger 26 provides an artificial facet joint 127. The outrigger 26 includes first and second rods 128 and 130 respectively connected to first and second plate members 22 and 24. The first and second rods 128 and 130 each mount respective first and second posts 132 and 134 having respective, mating, complementally configured first and second facets 136 and 138 on the posts. A retaining skirt 140 encloses the first and second facets 136 and 138.

The first and second rods 128 and 130 each include a connector 142 for attachment to the plate members at one end and a coupler 144 for attachment to the posts at the other end. The connectors 142 permit removable fastening of the rods to respective ones of the plate members 22 and 24. In the preferred embodiment illustrated in the drawings, the connectors 142 include a threaded pin 146 received in a tubular cannula 148 of each rod 128 and 130. The tubular cannula 148 each have a slotted tip 150 distal to the coupler 144 for insertion into the recesses 92 and 124. The slotted tip 150 includes a plurality of finger-like extensions 152 each having an enlarged, bulb-like end 154. The cannula 148 have an enlarged, rounded knuckle 156 at the proximate end 158 adjacent to and received by the coupler 144, and an externally threaded barrel 160 intermediate the tip 150 and the rounded knuckle 156. The tubular cannula 148 also have internal walls 162 defining a passage 164 for receiving the threaded pin 146 therein. As may be seen in FIG. 8, for example, the initial configuration of the passage 164 interior of the slotted tip 150 is convergent in a direction from the coupler toward the tip 150, such that the diameter of the bulb-like end 154 is initially approximately the same as the unthreaded portion 166 of the tubular cannula remote from the threaded barrel 160. At least a portion 168 of the internal walls 162 also have threads 170 thereon. The rounded knuckle 156 is rounded along its distal surface, and includes at its proximate surface slots 172 or other tool-receiving slot or socket such as for receiving a hex or other wrench to permit driving and removal of the tubular cannula 148. The threaded pin 146 is complementally sized for axial insertion into the passage 164 and has threads 174 thereon for permitting advancement and removal of the pin from the tubular cannula 148. The pin 146 preferably includes a shank 176 and a head 178, one of which is provided with the threads 174. As illustrated, the head 178 is externally threaded for engagement with the threads 170 of the tubular cannula 148. The head 178 also includes a hex socket 180 or similar structure whereby a tool, such as a screwdriver or an Allen wrench, may be inserted for advancing the pin 146 into the tubular cannula 148. The coupler 144 preferably is provided as a multi-axial head 182 and includes a collar 184 having arcuate inner walls 186 which are sized and configured to receive the rounded knuckle 156 in snap-on engagement, whereby once a tubular cannula 148 is inserted into the multi-axial head 182 with the rounded knuckle 156 installed in the collar 184, the rounded knuckle 156 may swivel and pivot within collar 184. The multi-axial head 182 further includes opposed ears 188 and 190 having internally facing opposed teeth 192 thereon. The opposed teeth 192 serve both to grip a post inserted between the ears 188 and 190 and to threadably receive a locking cap 194.

The first and second posts 132 and 134 are inserted between the ears 188 and 190 whereby their respective first and second facets 136 and 138 are in opposed engagement. The facets 136 and 138 are complementally configured, one facet having a generally concave mating surface 198 and the other having a convex mating surface 196 and both being inclined in a superior to inferior direction. It is to be understood that either the superior facet 136 or the inferior facet 138 may have either a convex or a concave face, but as illustrated the convex mating surface 196 is provided on the superior facet while the concave mating surface 198 is provided on the inferior facet 138. Retaining skirt 140 is provided over the facets 136 and 138 to aid in their initial retention. The skirt 140 is preferably tubular (shown bisected in FIG. 12) and provided of a flexible, resilient and biologically inert synthetic resin material. The skirt may be held in position by clamps 200, drawstrings, resilient bands at each end, or by its own resiliency, for example. For ease of use, the posts including the facets may be provided already connected by the skirt 140 so that the surgeon need not assemble the skirt around the facets during surgery.

Figure 4:
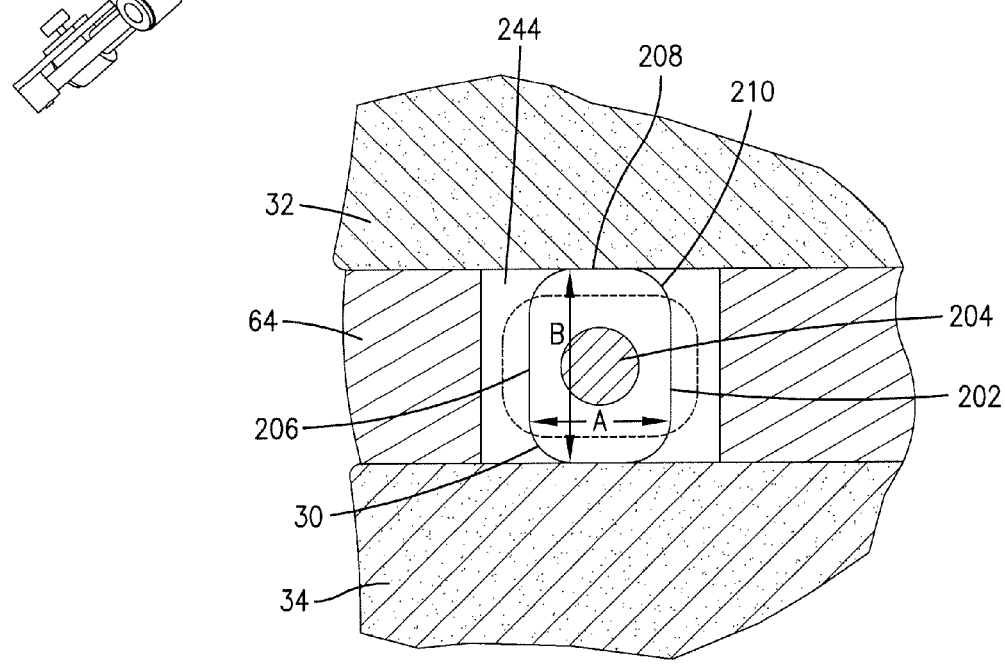
FIG. 4 is an enlarged, fragmentary vertical sectional view taken along line 4-4 of FIG. 3, showing the spacer in position between adjacent vertebrae before insertion of the plate members.

In order to facilitate insertion of the artificial disc 20 between the vertebrae, and because of possible compression of the natural disc 64, it may be necessary to provide additional spacing therebetween. Additional space between adjacent vertebrae may be provided by spacer 30 shown in FIG. 4. The spacer 30 is configured for insertion in a tunnel initially cut in the natural disc 64. The spacer 30 includes a block 202 connected to an elongated handle 204. The block 202 is generally rectangular in transverse shape, having a primary dimension A which is smaller than a secondary dimension B transverse thereto, parallel long sides 206 and parallel short sides 208 perpendicular to the long sides 206, and rounded corners 210 which facilitate turning of the spacer 30 between the vertebrae.

Figure 7:
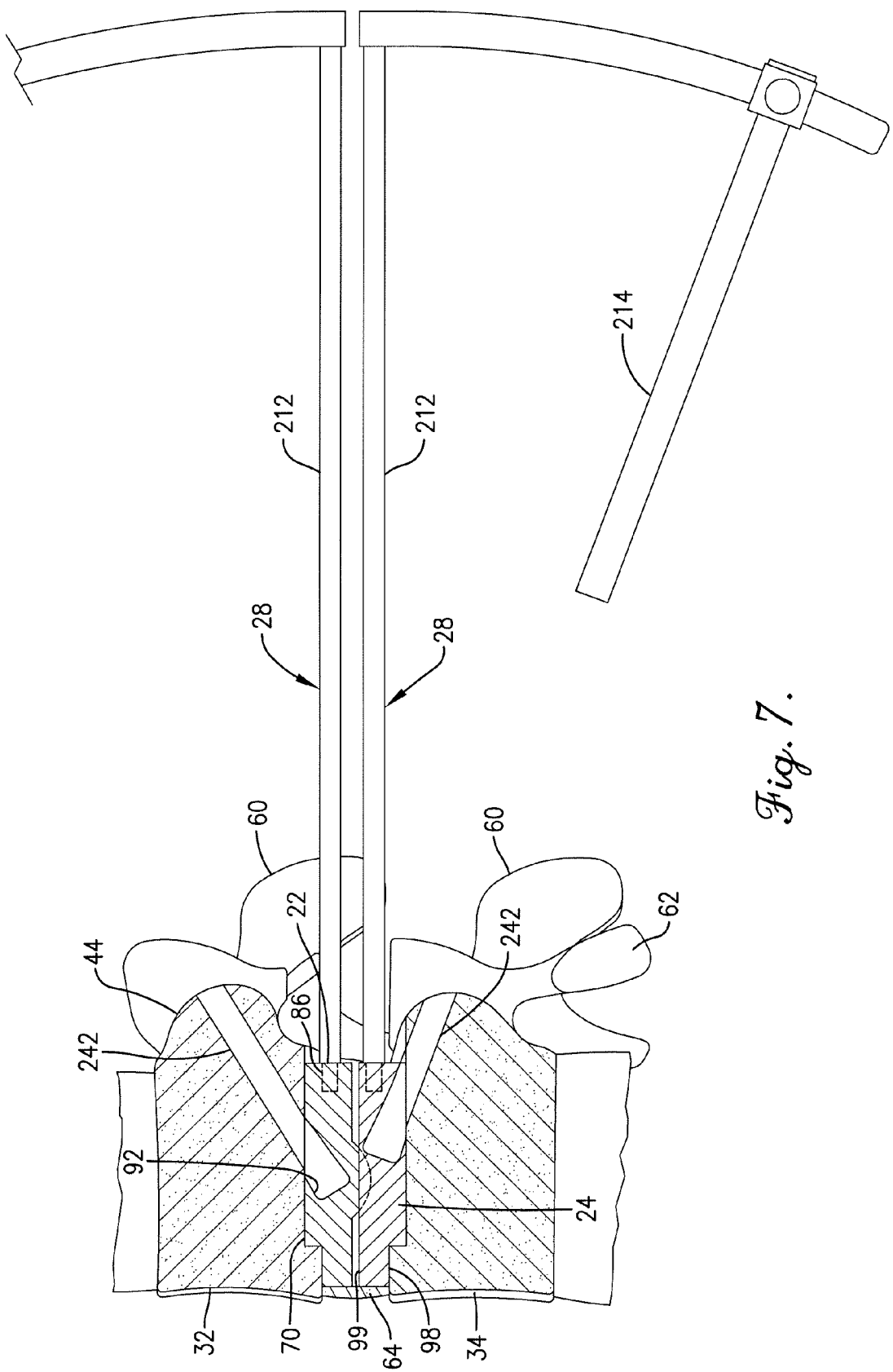
FIG. 7 is a fragmentary vertical cross-sectional view through a portion of the spine showing the channels drilled in the pedicles of the vertebrae in alignment with the openings in the plate members.

Further, the tool 28 of the present invention is provided to aid the surgeon installing the artificial disc with regard to aligning the drill for drilling channels in the pedicles for the rods of the outrigger 26. As shown in FIG. 7, the surgeon may employ one tool 28 sequentially or use two tools 28 on respective ones of the plate members 32 and 34. The tool 28 broadly includes a carrier 212, and a drill guide 214, and is preferably made of a corrosion-resistant metal such as stainless steel.

Carrier 212 is preferably provided to include a slide 216 and an elongated rod 218 having a threaded stem 220 at one end thereof, the threaded stem being sized and configured for threading into the longitudinally extending holes 86 and 116 in the back edges of each of the plate members 32, 34. However, it may be appreciated that the stem 220 and its receiving longitudinally extending holed 86 and 116 could be smooth, or polygonal, may be provided with a snap connection, or other mounting configurations for holding the tool 28 temporarily on the respective plate member. The opposite end of the elongated rod 218 is provided with a mounting section 222 for receiving the slide 216. The mounting section 222 may be threaded or include a snap connection. In the embodiment illustrated, the mounting section 222 is provided as a flat-sided flange 224 for receiving the protractor thereon. The slide 216 includes a coupler 226 complementally configured with the mounting section 222 for facilitating coupling of the arcuate-shaped slide to the rod 218, and a beam 228. The beam 228 is preferably arcuate in configuration, with the coupler 226 preferably laterally offsetting the beam 228 relative to the rod 218. A set screw 230 may be provided to act as a securement to hold the mounting section 222 to the rod 218. The drill guide 216 includes an elongated tube 232 and a slider 234. The slider 234 mounts the tube 232 thereon and includes structure defining a slot 244 which is complementally configured to the beam 228 so that the drill guide 216 fits snugly to the beam but the position of the slider 234 may be adjusted along the beam. The tube 232 has a central axis A, and advantageously, the central axis A will always orient toward the recess in the rib of the respective plate member 22, 24 to which the tool 28 is mounted, such that the central axis A always intersects at the same point as the drill guide is shifted along the beam 228 of the carrier 212. The slider 234 offsets the tube 232 relative to the beam 228 so that there is no interference between the beam and the tube 232, and also whereby the tube 232 is substantially co-planar with the carrier 212. A thumbscrew 236 or other fastener may threaded through a companion opening in the slider 234 if additional securement to hold the drill guide stationary in use is necessary. The tube 232 is sized to receive a drill bit 238 attached to a drill 240, the diameter of the tube 232 and the drill bit 238 preferably being sized so that a channel 242 created by the drill bit 238 is substantially of the same diameter as the outside diameter of the unthreaded portion 166 of the rods as seen, for example, in FIG. 9.

A desired method of insertion of the artificial spinal disc 20 of the present invention is also provided. After initial incisions and spreading of the skin and muscles to gain access to the spinal region from a posterior direction (preferably with the patient in a supine position, the surgeon cuts away a portion of the inferior articular process 56 of the first vertebra 32 and a portion of the superior articular process 52 of the second vertebra 34 immediately therebeneath in order to provide a route for the introduction of the plate members 22 and 24 therethrough. The surgeon then cuts a tunnel 244 into the natural disc of the patient of a width substantially corresponding to the width of the plate members between the respective side edges of one panel 78 and 80 and 108 and 110 of the other panel. If the spacing between the first vertebra 32 and the second vertebra 34 have been reduced to too great an extent, the block 206 of the spacer 30 is inserted into the tunnel 244 in an initial position as shown in dashed lines in FIG. 4. The block 206 is then turned 90° to the position indicated in solid lines in FIG. 4 to cause additional space to be created between the first vertebra 32 and the second vertebra 34. The spacer may then be removed. Thereafter, a chisel or similar tool is used to cut troughs 246 and 248 into the body 40 of each of the vertebra 32 and 34. The troughs 246 and 248 oppose one another and are oriented in a parallel direction to the tunnel and preferably substantially centered laterally. Further, the troughs 246 and 248 are sized to receive respective ribs 70 and 110.

Figures 5, 6:
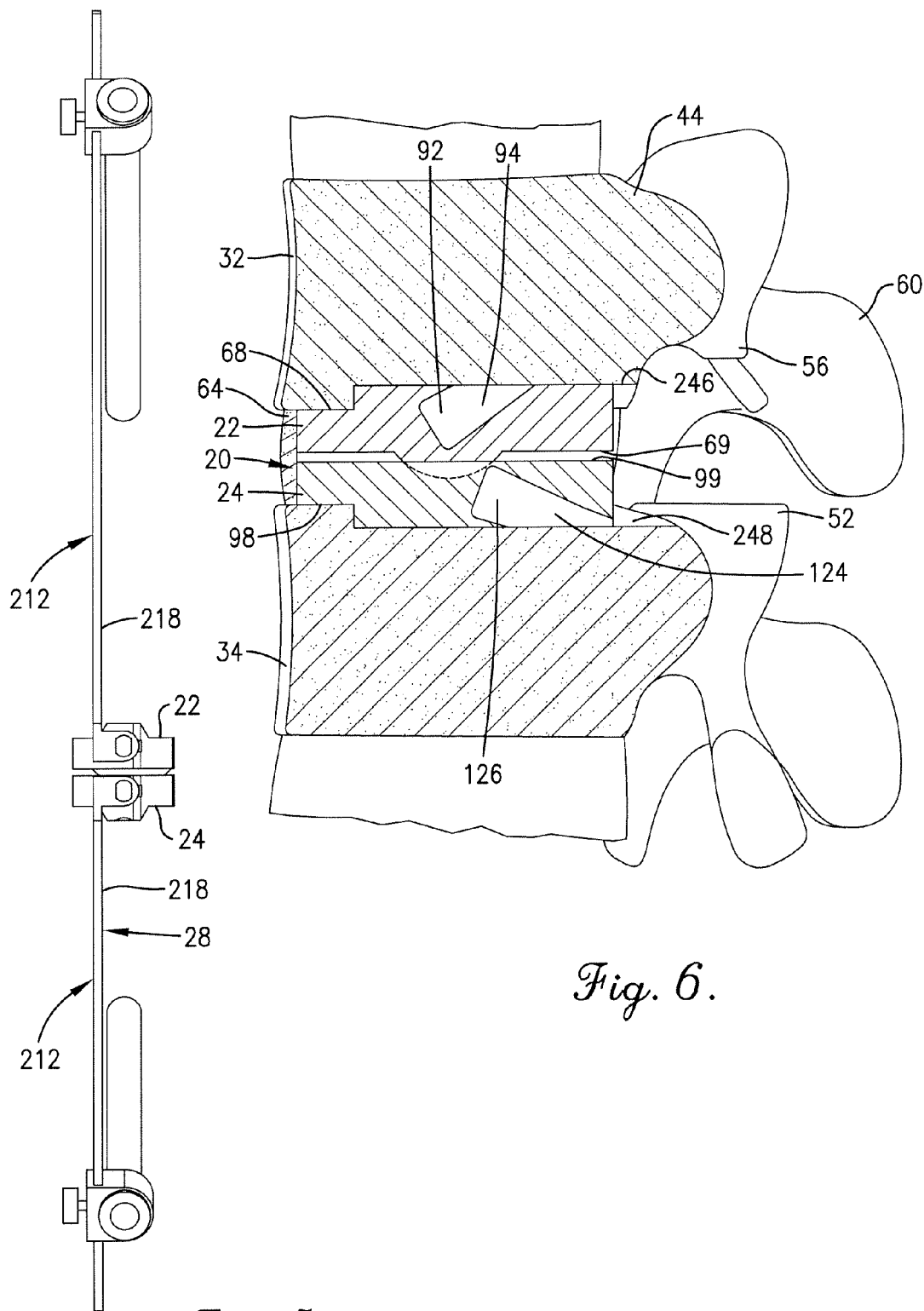
FIG. 5 is a end elevational view showing the tool attached to the plate members.
FIG. 6 is an enlarged, fragmentary vertical cross-sectional view taken along line 6-6 of FIG. 3, showing the artificial disc plate members having complemental weight-bearing surfaces and recesses for receiving the rods of the outriggers.

The surgeon then places the plate members 22 and 24 in mating juxtaposition with one another whereby the bearing 72 is received in the bearing receiving depression 102. The surgeon then slides the assembled plate members 22 and 24 into the tunnel 244 with the ribs 70 and 110 received in and sliding along respective trough 246 and 248 until the center of the bearing is located substantially at the load bearing axis of the spinal column in the region between the first vertebra 32 and the second vertebra 34 as illustrated in FIGS. 1, 3 and 6. It may thus be appreciated that the surgeon is employing a substantially unilateral approach from the posterior direction. In addition, the ribs 70 and 110 act both as a guide during insertion of the plate members 22 and 24 but also provide additional stabilization to minimize movement of the artificial disc off of the weight bearing axis of the spinal column. Further, a substantial portion of the natural disc of the patient is left intact for additional cushioning and support and the bone ingrowth coating or surface on the plate members 22 and 24 should help promote natural fixation of the artificial disc 20.

Because the natural facet joint between the adjacent inferior articular process and the superior articular process on one side of the first vertebra 32 and the second vertebra is lost as a result of the insertion of the plate members 22 and 24 from one side in a posterior position, the present invention provides the outrigger 26 to provide an artificial facet joint. After the plate members 22 and 24 are in place, the surgeon then attaches the tool 28 to the plate members 22 and 24 by affixing the carriers to the holes 86 and 116 as shown, for example, in FIGS. 2, 3, 10 and 11. The surgeon moves the drill guide 216 along the beam of the slide 216 until the channel 242 to be drilled is aligned to pass through substantial bone mass through the pedicle 44 on the desired side of each of the first vertebra 32 and the second vertebra 34. Beneficially, the drill guide 216 remains aligned with the entry of recesses 92 and 124 along the top of the ribs so that the surgeon will need to be concerned only with finding the appropriate bone mass in the pedicle knowing that the drill guide will align the drill bit with the respective recess 92 or 124 without it being seen. The surgeon then inserts the drill bit 238 into the tube 232 and drills the channel 242 through the pedicles 44 on one side of each of the first vertebra 32 and second vertebra 34 for receiving the rods 128 and 130. With the channels thus drilled as shown in FIG. 7, the tool 28 may then be removed from the plate members 22 and 24.

Figure 8:
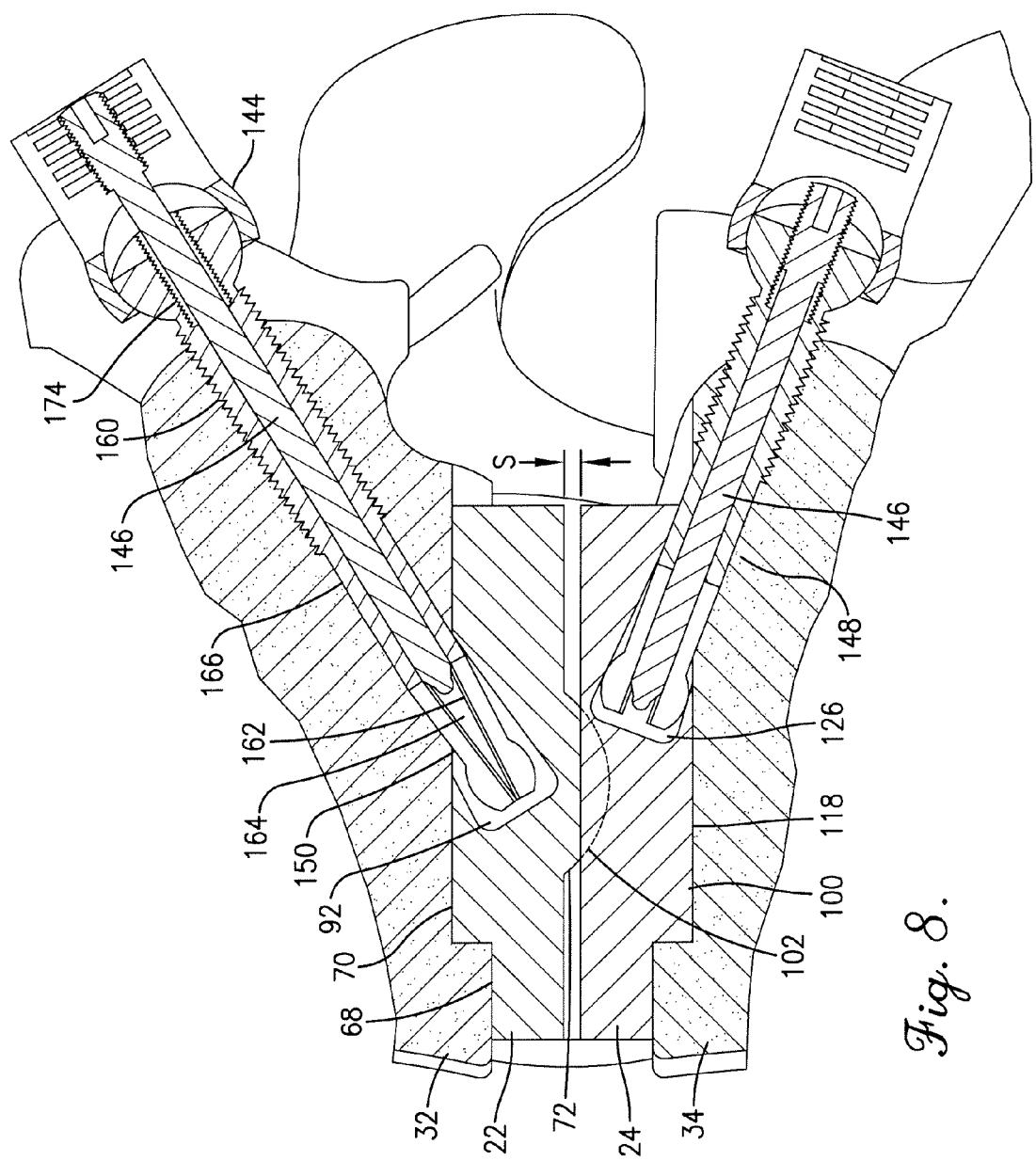
FIG. 8 is an enlarged, fragmentary vertical cross-sectional view similar to FIG. 7 but showing the rods of the outriggers inserted in the channels, with the upper rod shown prior to expansion in the recess and the lower rod after expansion, and with multiaxial gripping heads mounted on the rods.

The rods 128 and 130 are then mounted on their respective ribs 70 and 110 of the plate members 22 and 24 as illustrated by FIG. 8. The surgeon initially inserts the rod as shown with respect to rod 128 in FIG. 8. While the threads may be omitted from the externally threaded barrel 158 on the exterior of the rods, the threads thereon aid in holding the rod in position. Additional attachment support is provided by advancing the pin 144 along the passage. As the pin 146 advances, the extensions 152 of the slotted tip 150 expand so that the bulb-like ends 154 spread and engage the inner surfaces 94 and 126 of the frustoconically shaped recesses 92 and 124, respectively. Because of the recesses 92 and 124 have a slightly greater transverse dimension at their end wall as opposed to their entry opening on the surface of the rib, the bulb-like ends 152 expand and help lock the rods in place once the pins are fully seated as shown in FIG. 9.

With the rods 128 and 130 fully inserted as desired, the surgeon then installs the posts 132 and 134 onto the multi-axial head 182 by positioning the posts between the gripping surfaces of the ears 190 and 192 of each multi-axial head. As may be seen in FIG. 9, the multi-axial heads 182 permit pivoting and rotation of the ears so that the posts 132 and 134 may be in superposed alignment, with the facets 136 and 138 in mating concave-convex relationship. The posts may be secured in this position further by threading thereon the locking cap 194 as shown in FIG. 9. Any excess length of the posts 132 and 134 extending beyond the multi-axial heads 182 may be cut away by the surgeon. The primary weight to be carried along the spinal column will pass between the plate members, with the facets 136 serving as a limiter against excessive twisting or vertical movement rather than for bearing weight. The skirt 140 being preplaced around the facets 136 and 138, the incision may be closed in accordance with ordinary surgical procedures.

Among the many benefits provided by the present invention are the minimization of risk of damage to the spinal cord by adopting a posterior, trans-pedicular approach from the side, the fact that one side of the vertebrae involved are left alone because of the unilateral approach which is minimally invasive, minimizing the possibility that the artificial disc will spin or shift one inserted in position, retaining substantial flexibility in the joint to avoid transferral of stress to other vertebrae, and the ability to leave the anterior ligament intact.

One further benefit of the present invention is that should the need arise, the artificial disc 20 hereof may be readily removed from the patient. By using threaded connections and a unilateral approach, if fusion of the adjacent vertebrae later becomes necessary, the entire artificial disc hereof may be removed. First, to remove the outrigger 26, the surgeon removes the locking caps 194 from the multi-axial heads and prises the posts 132 out from between the ears 190 and 192. The surgeon may then gain access to the pin within the tubular cannula, and using a wrench or similar tool, back out the threaded pin from the tubular cannula in which it is received. Because the rounded knuckle 156 includes slots 172 or other tool receiving structure, once the pin 146 is backed out, the extensions 152 of the slotted tip 150 are free to collapse as the tubular cannula is threaded out of the bone and the tip 150 is withdrawn from the respective recess. With the rods removed, the surgeon may insert threaded bolts or other tools into the holes 86 and 118 to use to gain a purchase on the plate members and remove them along the tunnel initially cut through the natural disc. Alternatively, if it was necessary to fix the first vertebra 32 against movement relative to the second vertebra, the plate members 22 and 24 could be left in position, but a solid bridge-type structure inserted either between the multi-axial heads or be attached between the plate members 22 and 24 and connected by threaded fasteners inserted into the holes 86 and 116.

As an alternative to the flexible retaining skirt 140 illustrated in FIGS. 9 and 12, a collar 250 may be utilized in connection with the artificial facets 136*a* and 138*a*. The collar 250 is initially manufactured having an upper cap 252 and a lower housing 254 which receive the posts 132 and 134 respectively. The post 132 passes through an access 256 in the upper cap 252 and the post 134 passes through an opening 258 in the lower housing 254. The access 256 generally presents a greater clearance between the collar 250 and the post 132 than the clearance between the collar 250 and the lower post 134 provided by opening 258 as illustrated in FIGS. 13 and 14. The upper cap 252 and lower housing 254 are then assembled and secured by welding, mechanical fasteners or the like along their respective mating edges so that the facets 136*a* and 138*a* are retained within the assembled collar 250, which is thereby provided as a unit along with the posts 132 and 134, so that the assembly including the collar 250 enclosing the artificial facets 136*a* and 138*a*, along with the posts 132 and 134, is provided to the surgeon ready for installation on the respective rods. Preferably, the lower post 134 is secured to the housing 254 at the opening 258 by welding, adhesive or a mechanical fastener so that no relative motion is permitted between the lower post 134 and the housing 254.

The collar 250 is configured with an inner wall 260. The inner wall 260 has a side surface 262 which is preferably generally arcuate in horizontal cross section, and most preferably, the side surface 262 which is generally ovoid in horizontal cross-section, being substantially circular in cross section along an anterior portion 264 and more prolate or eccentrically shaped along a posterior portion 266 as illustrated by FIG. 15. The inner wall 260 also closely conforms to the respective outer surfaces 268 and 270 of the facets 136*a* and 138*a* but permits limited relative movement therebetween. Most preferably, the inner wall 260 includes an upper wall surface 272 which is positioned closely adjacent an upper margin 274 of the superior facet 136*a* so that the mating, convex and concave faces 196 and 198 of the facets 136*a* and 138*a* are maintained in constant engagement and the facets do not separate when in the full distraction position as shown in FIG. 13. Moreover, the side surface 262 is most preferably substantially upright and perpendicular to the upper wall surface 272 along the anterior portion 264, but the posterior portion 266 is slightly inclined so as to present a more conical configuration when viewed in vertical cross-section as seen in FIGS. 13 and 14. The outer surface 270 of the inferior facet 138*a* is preferably provided with a lip 278 which extends posteriorly so that in horizontal cross-section, it has an ovoid shape complemental to and closely adjacent the inner wall 260, as seen in FIG. 15. The outer surface 268 of the superior facet 136*a* is preferably generally ovoid in cross-section, such that the anterior side 280 of the superior facet 136*a* is generally circular while the posterior side 282 is prolate and more closely conforms to the configuration of the inner wall 260, having a generally tapered posterior side 282 such that the distance of the posterior side 282 from the anterior portion 264 of the inner wall 260 increases in a downward direction away from post 132. The configuration of the upper facet 136*a* relative to the collar 250 is such as to limit separation between the facets 136*a* and 138*a*, but still providing sufficient clearance between the posterior side 282 of the outer surface 268 of the superior facet 136*a* and the posterior portion 266 of the inner wall 260 to permit limited sliding of the superior facet 136*a* downwardly along the inferior facet 138*a* and limited relative rotational movement of the superior facet 136*a* relative to the inferior facet 138*a*.

The relative configurations of the collar 250 and the facets 136*a* and 138*a* provide improved stability while permitting limited relative movement between the posts 132 and 134 and their respective facets 136*a* and 138*a* in the artificial spinal disc 20 hereof. FIG. 13 shows the position of the posts and facets 136*a* and 138*a* when the facets are in their fully distracted position. As patient moves (as illustrated here, bends so that the upper vertebra 32 moves clockwise relative to the lower vertebra 34), the superior facet 136*a* is permitted to slide downwardly along the inferior facet 138*a* until the outer surface 268 engages the side surface 262 of the inner wall 260, thereby limiting the amount of relative movement between the facets 136*a* and 138*a*, and also providing additional stability for the patient. As the upper facet 136*a* moves beyond the position shown in FIG. 14, the outer surface 268 will engage the inclined posterior portion of the side surface 262 of the inner wall. The extended lip on the inferior facet 138*a* enables the concave and convex mating surfaces to substantially remain in contact and provide continuous support in the region as well as continuous resistance so that the patient does not experience rapid slippage as the frictional engagement changes.

In addition, a limited amount of relative rotational movement is permitted between the facets 136*a* and 138*a*. FIGS. 14 and 15 illustrate that as the superior facet 136*a* begins to rotate relative to the inferior facet 138*a*, the generally convex mating surface or face 196 begins to ride up along the opposing, and fixed, concave mating face 198 of the inferior facet 138*a*. When the upper facet 136*a* shifts down along the lower facet 138*a*, an axis A of the inferior post 132 remains stationary, while the axis B of the superior post 134 moves off of its initial alignment with axis A in a generally anterior to posterior direction. As shown in FIG. 15, when the upper facet 136*a* also has limited rotational movement relative to the lower facet 138*a*, the axis B also moves to one side of an anterior to posterior plane bisecting the lower facet 138. The upper facet 138*a* is permitted to continue this relative rotational movement as the patient twists until the outer surface 268 of the superior facet 136*a* moves into engagement with the side surface 262 of the inner wall 260 of the collar 250. The combination effect of the convex and concave face engagement with the camming effect when the upper facet engages the inner wall provides increased resistance as the patient's torso twists up to the point of engagement, as well as a beneficial centering function.

Advantageously, the configuration of the facets 136*a* and 138*a* and the collar 250 is complemental and synergistic in regard to limiting the amount of patient movement. That is to say, the more movement the patient undertakes to cause the upper facet 136*a* to slide downwardly along the lower facet 138*a*, the less relative rotational movement is permitted. This is because when the upper facet 136*a* fully slides downwardly, it comes into full engagement with the side surface 262 so that no relative rotational movement is permitted. This inhibits excessive movement which might lead to injury to the patient. Thus, the configuration of the inner wall 260 benefits the patient in which the artificial spinal disc has been implanted by permitting some movement, but also by limiting the amount of movement based on a combination of physical factors related to how much stress the patient is placing on the spinal region.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention. By way of example only, the rods of the outrigger 26 could be attached to the plate members by threading or other means of fastening, a separate synthetic resin or metal member could be used as a weight bearing member between the plate members each having a generally convex bearing receiving surface, and a bio-ingrowth surface coating could be applied to the exterior of the rods to promote bone growth therearound. In addition, the collar 250 could have a tapered inner wall to allow sliding movement while maintaining contact with the facets, could be configured with a generally cylindrical inner wall 260, or both facets could be free to move relative to the collar. It is also to be understood that the plate members could be configured to receive additional outriggers whereby both natural facet joints could be removed and artificial facets provided in lieu thereof.

The inventors hereby state their intent to rely on the Doctrine of Equivalents to determine and assess the reasonably fair scope of their invention as pertains to any apparatus not materially departing from but outside the literal scope of the invention as set out in the following claims.

The invention claimed is:

1. An apparatus for attaching an outrigger to an artificial spinal disc, said artificial spinal disc being for location within an intervertebral space between first and second adjacent vertebra, said space normally occupied by a natural spinal disc, said apparatus comprising:
    an artificial spinal motion preservation disc configured to preserve motion when implanted in an intervertebral space;
    a carrier including an arcuate segment fixed on the distal end of the carrier;
    a tubular drill guide operably coupled with the arcuate segment and continuously translatable there along for radial travel of the tubular drill guide in a cephalad/caudal direction; and
    a connection structure operable to detachable connect the carrier with the artificial disc,
    wherein the connection structure coupled the carrier to the artificial disc, and
    wherein said drill guide includes a tubular member having a central axis, and
    wherein said central axis of the tubular member continuously intersects a common point as said drill guide is translated along said carrier in a cephalad/caudal direction, and
    wherein the common point spatially intersects with a position on the artificial disc,
    wherein the artificial disc comprises a bore disposed on an outer surface of the artificial disc, and the common point spatially intersects with a position in said bore.

2. An apparatus as set forth in claim 1, wherein the arcuate segment has a fixed end and a free end, and the carrier further comprises a radially extending elongated body having first and second ends; wherein
    the first end of the radially extending elongated body is affixed to the fixed end of the arcuate segment.

3. An apparatus as set forth in claim 2, wherein the connection structure is disposed at the second end of the radially extending elongated body.

4. An apparatus as set forth in claim 1, wherein said drill guide includes a tubular member having a central axis, and wherein said central axis of the tubular member continuously intersects a common point as said drill guide is translated along said carrier, and wherein the common point is spatially offset from the radially extending elongating body.

5. An apparatus as set forth in claim 4, wherein the radially extending elongated body defines a longitudinal axis extending along its length, and the common point is spatially offset from the longitudinal axis defined by the radially extending elongated body.

6. An apparatus as set forth in claim 1, wherein the connection member comprises a threaded member.

7. An apparatus as set forth in claim 4, wherein the connection member comprises a threaded member.

8. An apparatus as set forth in claim 1, wherein the artificial disc comprises a pair of adjacent plate members.

9. An apparatus as set forth in claim 8, wherein the adjacent plate members are configured to articulate relative to one another for preserving motion when implanted in an intervertebral space.

* * * * *